US012725712B2

(12) United States Patent
Hazak et al.

(10) Patent No.: US 12,725,712 B2
(45) Date of Patent: Sep. 1, 2026

(54) SYSTEM AND METHOD FOR CHRONIC PAIN MANAGEMENT

(71) Applicant: EQUANIMITY LTD., Ramat-Gan (IL)

(72) Inventors: Samuel Hazak, Rehovot (IL); Erez Levanon, Ramat-Gan (IL)

(73) Assignee: EQUANIMITY LTD., Ramat-Gan (IL)

(*) Notice: Subject to any disclaimer, the term of this patent is extended or adjusted under 35 U.S.C. 154(b) by 2 days.

(21) Appl. No.: 18/787,075

(22) Filed: Jul. 29, 2024

(65) Prior Publication Data

US 2025/0069756 A1 Feb. 27, 2025

Related U.S. Application Data

(60) Provisional application No. 63/533,912, filed on Aug. 22, 2023.

(51) Int. Cl.
*G16H 50/30* (2018.01)
*G16H 10/60* (2018.01)

(52) U.S. Cl.
CPC ............. *G16H 50/30* (2018.01); *G16H 10/60* (2018.01)

(58) Field of Classification Search
CPC ......... G16H 50/30; G16H 10/60; G16H 15/00
See application file for complete search history.

(56) References Cited

U.S. PATENT DOCUMENTS 11,367,519 B1 * 6/2022 Heldman ............... G16H 40/63
12,380,980 B1 * 8/2025 Heldman ............... G16H 20/10
2009/0105550 A1 * 4/2009 Rothman ............... G16H 50/30 600/300
2017/0228517 A1 * 8/2017 Saliman ................. G16H 10/20
2019/0189259 A1 * 6/2019 Clark ..................... G16H 10/60
2020/0273583 A1 * 8/2020 Jain ........................ G16H 10/20
2021/0296000 A1 * 9/2021 Shaw ................ G06Q 30/0202
2022/0125386 A1 * 4/2022 Marras .................. A61B 5/1114
2022/0384046 A1 * 12/2022 Saliman ................. G16H 10/60
2025/0037867 A1 * 1/2025 Bharmi .................. G16H 50/30

(Continued)

OTHER PUBLICATIONS

Patterson DG, Wilson D, Fishman MA, Moore G, Skaribas I, Heros R, Dehghan S, Ross E, Kyani A. Objective wearable measures correlate with self-reported chronic pain levels in people with spinal cord stimulation systems. NPJ Digit Med. Aug. 15, 2023;6(1):146. doi: 10.1038/s41746-023-00892-x. PMID:37582839 (Year: 2023).*

(Continued)

*Primary Examiner* — Sun M Li
(74) *Attorney, Agent, or Firm* — The Roy Gross Law Firm, LLC; Roy D. Gross

(57) ABSTRACT

Methods and systems for monitoring and displaying pain level of a patient including obtaining inputs comprising at least: a patient report of a pain level, a physical activity indicator obtained from at least one computing device associated with the patient, a sleep indicator obtained from the at least one computing device, and a social activity indicator obtained from the at least one computing device; analyzing the inputs to obtain at least three factor evaluations corresponding to at least three factors indicating a wellbeing status of the patient; integrating the at least three factor evaluations into a pain score assessment; and displaying the at least three factor evaluations and the pain score evaluation.

16 Claims, 7 Drawing Sheets

(56) References Cited

U.S. PATENT DOCUMENTS

2025/0046461 A1* 2/2025 Awasthi ................ G16H 10/60

OTHER PUBLICATIONS

Juckett DA, Davis FN, Gostine M, Reed P, Risko R. Patient-reported outcomes in a large community-based pain medicine practice: evaluation for use in phenotype modeling. BMC Med Inform Decis Mak. May 28, 2015;15:41. doi: 10.1186/s12911-015-0164-4. PMID: 26017305; PMCID: PMC4446111. (Year: 2015).*

W. Cui et al., "Text-to-Viz: Automatic Generation of Infographics from Proportion-Related Natural Language Statements," in IEEE Transactions on Visualization and Computer Graphics, vol. 26, No. 1, pp. 906-916, Jan. 2020, doi: 10.1109/TVCG.2019.2934785. (Year: 2020).*

Alpert JM, Kota NSP, Ranka S, Mendoza TV, Solberg LM, Rashidi P, Manini TM. A Simulated Graphical Interface for Integrating Patient-Generated Health Data From Smartwatches With Electronic Health Records: Usability Study. JMIR Hum Factors. Oct. 30, 2020;7(4):e19769. doi: 10.2196/19769. PMID: 33124988; (Year: 2020).*

Patterson DG, Wilson D, Fishman MA, Moore G, Skaribas I, Heros R, Dehghan S, Ross E, Kyani A. Objective wearable measures correlate with self-reported chronic pain levels in people with spinal cord stimulation systems. NPJ Digit Med. Aug. 15, 2023;6(1):146. doi: 0.1038/s41746-023-00892-x. PMID:37582839 (Year: 2023).*

* cited by examiner

PAIN SCORE: 84

PAIN SCORE: 40

520

SYSTEM AND METHOD FOR CHRONIC PAIN MANAGEMENT

CROSS REFERENCE TO RELATED APPLICATION

This application claims the benefit of priority of U.S. provisional patent application No. 63/533,912, filed Aug. 22, 2023, the contents of which are all incorporated herein by reference in their entirety.

TECHNICAL FIELD

The present disclosure relates to pain assessment, monitoring and management.

BACKGROUND

Pain is a distressing feeling which may be caused by intense or damaging stimuli. The International Association for the Study of Pain defines pain as "an unpleasant sensory and emotional experience associated with, or resembling that associated with, actual or potential tissue damage."

Acute pain is usually transitory, and lasts until the noxious stimulus is removed or the underlying damage or pathology has healed. In contrast, chronic pains, also referred to as "persistent pain", whether caused by a known reason or not, may persist for years. Traditionally, the distinction between acute and chronic pain has relied upon an arbitrary interval of time between onset and resolution, such as 3 months or 6 months since the onset of the pain.

Chronic pains are a widespread and growing phenomena. For example, it is estimated that in the US alone, over 100 million people suffer from chronic pains, and the cost of treating the chronic pains exceeds $1 trillion annually.

A serious challenge in pain monitoring and treating is that currently the source of information is uni-dimensional and subjective, being a report by the patient, usually in the form of a number in the scale of 0 to 10, with 0 being no pain at all, and 10 the worst unbearable pain. However, it is well known that such reports are not only subjective, but are also affected by multiple factors, wherein some of which are constant for the patient while others are changing. Such factors may include but are not limited to any one or more of the patient's current motivations, contexts, and experience, the general physical, mental and emotional wellbeing of the patient, the patient's family and social status, the relationship and trust with the clinic personnel and in particular the physician, healthcare professionals' perceptions and treatment goals.

In addition, the patient may knowingly or unknowingly change the pain level self assessment, to a higher or lower value, due to any one or more of the following reasons (or others): impression management; desire to appear tough, self consciousness or embarrassment, downplaying pain, fear or avoidance, concern for social networks, counteract overreporting, ensuring treatment or mediation or extra or more robust or accelerated treatment or mediation or dynamic appraisal, stigmas associated with pain or fear from being rejected from jobs or social activities, fear of future pain, and of one's pain reports not being taken seriously or trusted.

Thus, numerical pain ratings fail to convey the complexity of pain experience, and are also often not believed, both by healthcare professionals and the general public, who tend to think that people are actually in less pain than they report. One of the top reasons for the disbelief relates to how patients differentially use the scale and the patients' concerns about how pain reporting influences clinician perception and treatment.

Thus, absent an objective measure, it is hard for a physician to effectively assess and even more so monitor the patient's state over time, in order to suggest the best treatment and evaluate its effectiveness.

THE BRIEF DESCRIPTION OF THE SEVERAL VIEWS OF THE DRAWINGS

The present disclosed subject matter will be understood and appreciated more fully from the following detailed description taken in conjunction with the drawings in which corresponding or like numerals or characters indicate corresponding or like components. Unless indicated otherwise, the drawings provide exemplary embodiments or aspects of the disclosure and do not limit the scope of the disclosure. In the drawings.

Figure 4:
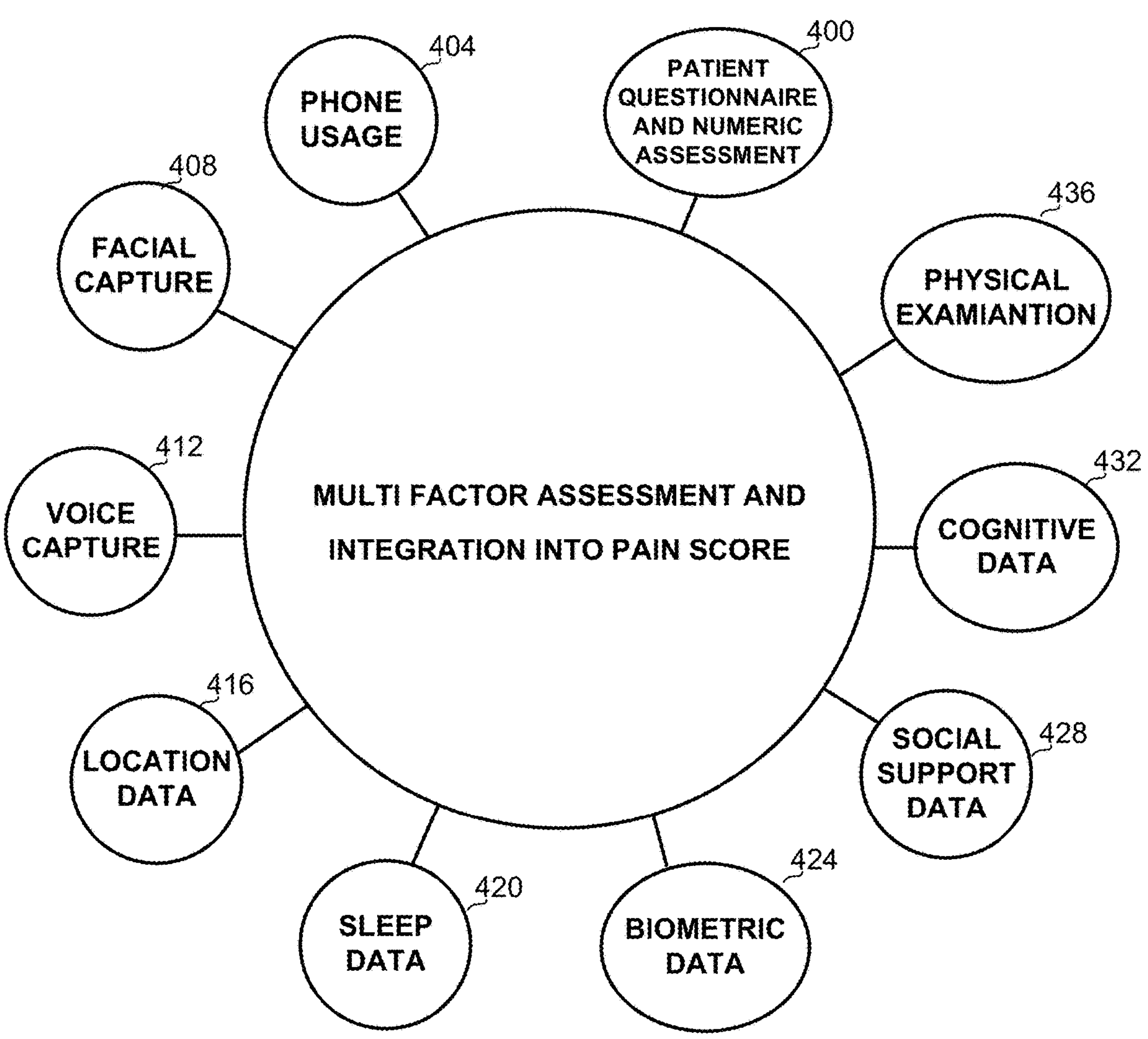
Figure 5:
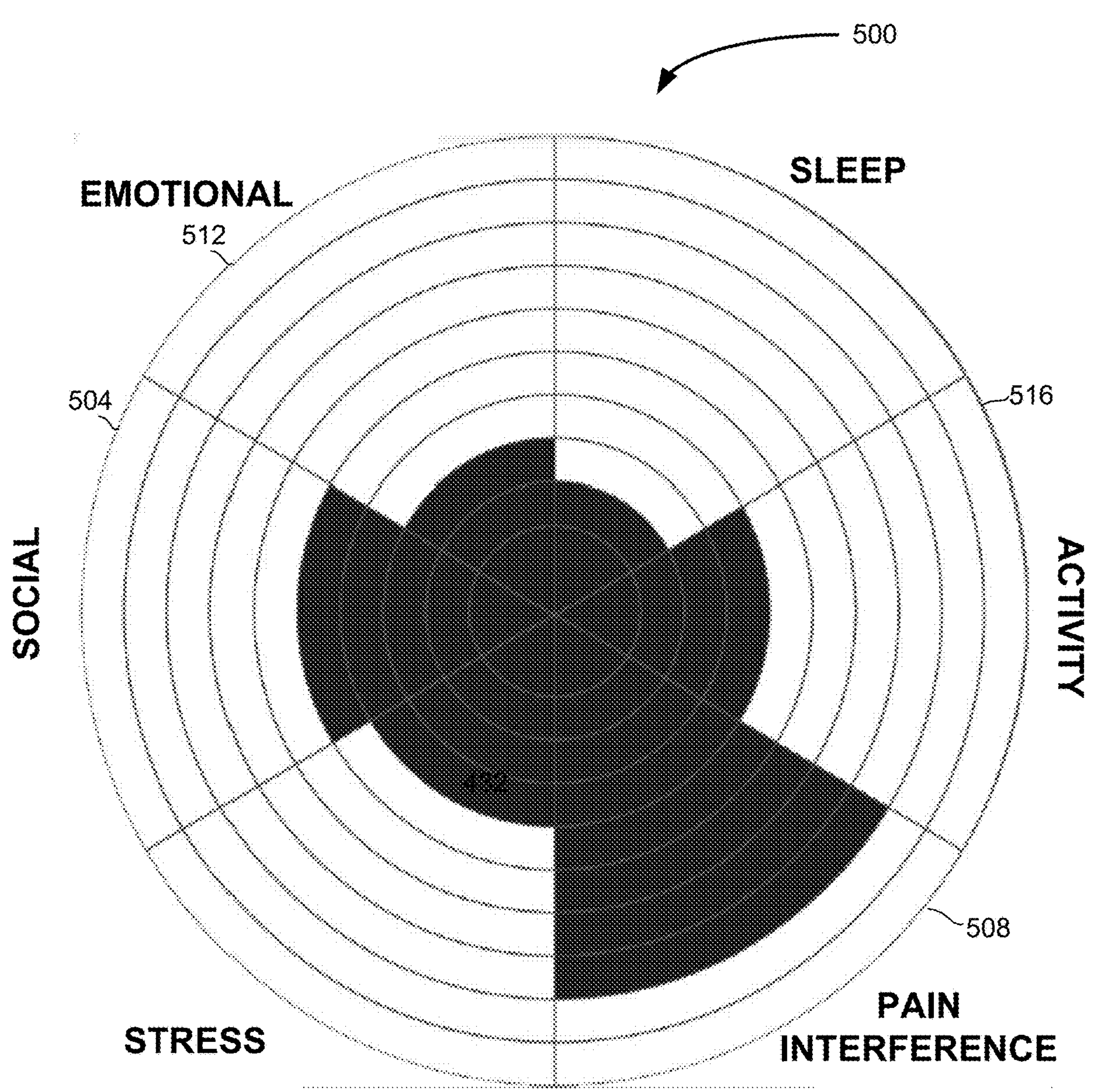
Figure 6:
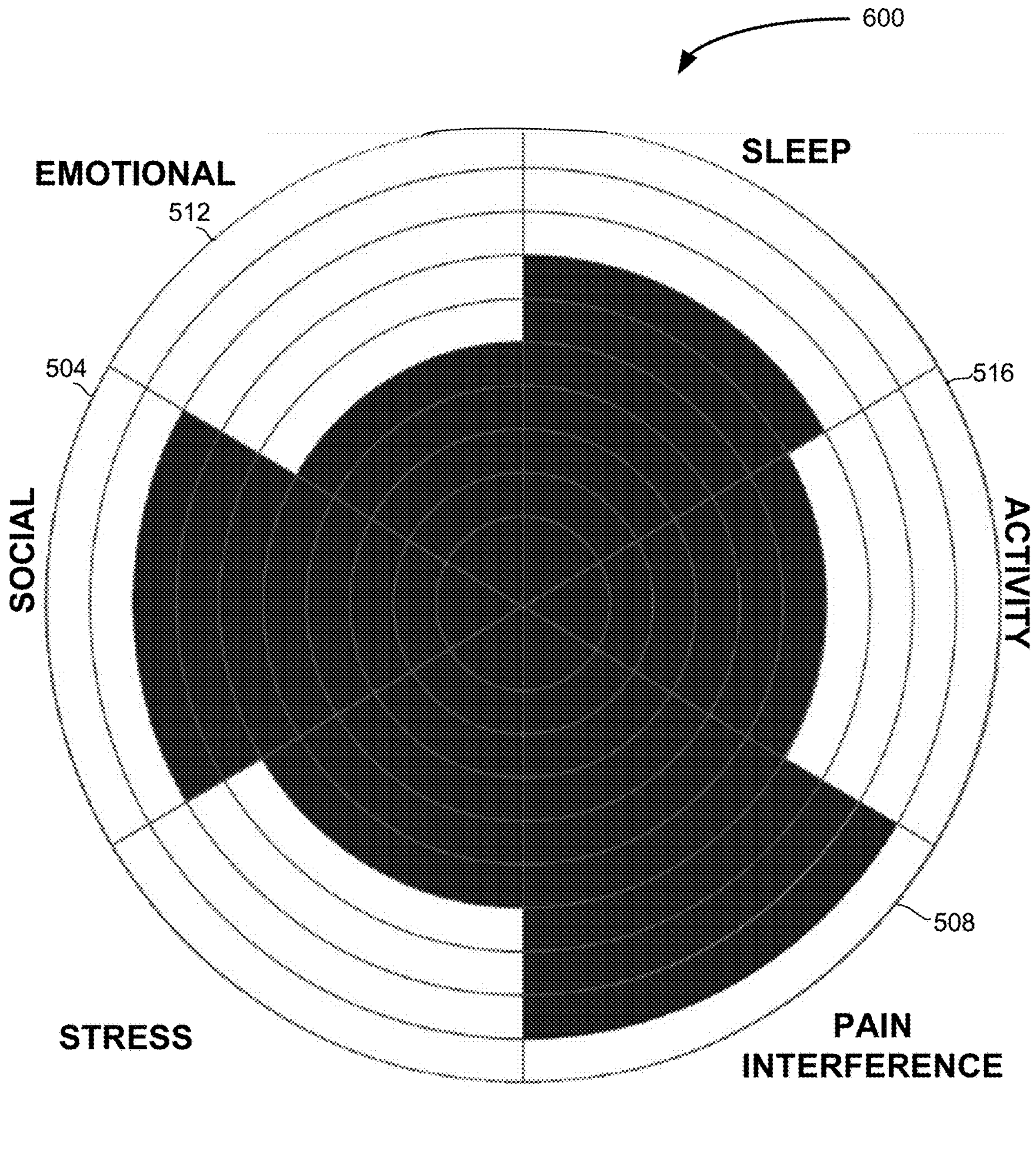
Figure 7:
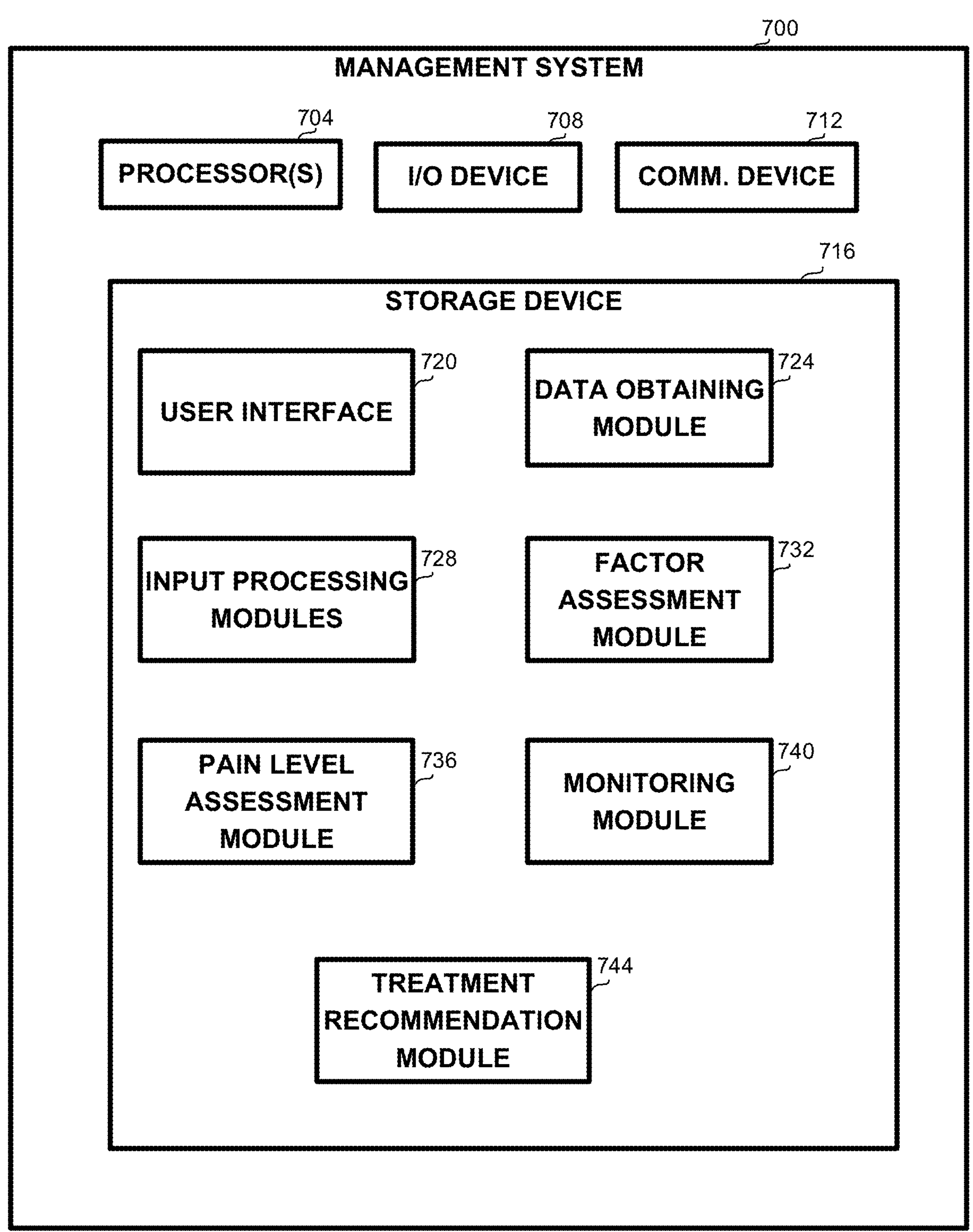

FIG. 4 illustrates the various types of the collected information, in accordance with some exemplary embodiments of the disclosed subject matter FIG. 5 and FIG. 6 show graphic representations of evaluated factors and assessed pain level, in accordance with some exemplary embodiments of the disclosed subject matter; and FIG. 7 shows a block diagram of a system for pain level evaluation and monitoring in accordance with some exemplary embodiments of the disclosed subject matter.

DETAILED DESCRIPTION

One technical problem dealt with by the disclosed subject matter is to establish a systematic manner for providing a personalized and objective pain measurement, such that an appropriate treatment can be prescribed.

Currently, pain level evaluation is based on user report, which is naturally subjective, and optionally on examination results which often provide no further useful information. Thus, the treatment of chronic pain is usually based on trial and error, and sometime general life advice such as "spend time with family and friends", "reduce stress", "reduce coffee consumption", or the like.

The reported pain level is significantly affected by multiple factors, including but not limited to: biological factors including current and past diseases, nociception, i.e., pain detection, inflammations, brain function, or the like; psychological factors such as mood, tendency to catastrophize, stress and copying; and social factors such as cultural factors, social environment, economic situation and social support. Thus, the pain level as reported by the patient is highly subjective and affected by multiple factors, wherein some of them may indeed related to the pain while others may not.

Thus, it is required to provide a method and system for obtaining personalized and objective pain measurement for a patient.

Another technical problem dealt with by the disclosed subject matter is the need to establish a monitoring and recommendation method and system, for monitoring the pain level and the factors over time.

Yet another technical problem dealt with by the disclosed subject matter is the need to make treatment recommendations and update them as required, based on the current pain measurement and the history, including the pain development, and the effect of tried treatments.

Yet another technical problem dealt with by the disclosed subject matter is the need to reduce the costs associated with pain management, including costly and repeating clinic visits, expensive tests and medications, or the like.

One technical solution of the disclosure comprises collecting information relevant to pain level evaluation from a variety of sources. The information may comprise the user's subjective assessment, as well as objective data. The data may be obtained from one or more devices, such as a mobile phone from which data related to the activity of the patient may be collected as well as additional information such as environmental data, voice and face/body captures of the patient and others.

Another source of information may be a wearable device capturing biological and environmental measurements of the patient, or the like. The information collected by a wearable device may include physiological indicators such as Heart Rate, Galvanic Skin Response (GSR) which may be used to determine the stress score, which may be good or bad depending on the situation, or the like. This information may be enriched with personal and environmental data, such as weather forecast or the patient's calendar, which may provide additional insight into the patient's day-to-day life and circumstances relevant to the measurement.

Some of the information may be collected on an ongoing basis, such as continuous measurement of biological aspects, or a mobile phone continuously storing the patient's activities. Other information types may be collected at constant or varying time periods, such as capturing the user's face or voice. Sleep parameters may be collected continuously when the user is sleeping or resting, or the like.

Additionally, the collected data may include a report by the user, but instead of a subjective unidimensional assessment of the pain level, a more detailed assessment questionnaire may be presented, which may be filled during the first use of the system to create a baseline, and optionally updated over time. The questionnaire may be scheduled automatically. For example, the questionnaire may be filled at the physician's office, at home before the visit, at predetermined time intervals, or the like. The questionnaire may relate to any one or more of the following points: medical history, subjective pain experience/symptoms, fear or avoidance estimation, mental state, level of daily functioning (physically, mentally, cognitively), pain Goals, Specific pain syndrome questions (such as CRPS, Fibromyalgia, etc.), pain diary, filled for example twice a day, events such as changes in pain levels, mood, activity, energy, sleep, or the like. In some embodiments, the patients may add input by friends, relatives, caregivers, or the like. The questionnaires, diary, event labelling or the like may allow the patient to convey the overall pain experience and the impact on the patient's life. Some questions may require numeric answers while others may be textual and analyzed by Natural Language Processing (NLP) tools. The questionnaire may be form-based, may use an interactive chatbot, audio or video interaction with a human, or the like.

The questionnaire may thus provide subjective but detailed integrated, personalized pain score and a lot of additional information, which may be used in evaluating the various factors and the pain level.

This collected information thus comprises unbiased, and objective information which may be used for creating a personalized profile and a baseline for comparison, as well as subjective information. The profile may later be used to determine the physiological as well as the biological and social aspect of the bio-psycho-social model and reduce the bias of the patients' subjective reports.

The collected information may then be preprocessed, in order to obtain useful information from the raw data. Each type of information may be preprocessed with corresponding tools. For example, captured voice may be preprocessed using voice analysis to analyze the emotional state of the user, such as whether the user is happy, stressed, angry, or the like. Captured face may be analyzed using image analysis to analyze whether the user seems painful, happy, stressed, or the like. The heartbeat and other biological measurements may be processed to identify a baseline and deviations therefrom, which can hint at stress, pain, or the like.

Processing of each of the data types may be performed by any engine, including but not limited to an Artificial Intelligence (AI) engine. The optional engine types may include but are not limited to any one or more of a Neural Network, a Deep Neural Network, a Convolutional Neural Network, Adversary Neural Network, or others. The engines may be trained using supervised or unsupervised training. For example, voice analysis may be performed by a classifier implemented as an AI engine trained upon voice examples labeled as stressed, angry, calm, happy or the like. The voice may be further preprocessed for noise removal, silence removal or the like. In another example, facial analysis may be performed by an AI engine trained upon face image examples labeled as happy, painful, neutral, or the like. Labeling may be performed by a human user, or by a pre-existing engine. In yet another example, heartbeat measurements may be examined to identify periods in which the heartbeat is faster than the normal. In yet another example, the phone usage may be analyzed to determine social activity, for example active participation in social networks, phone conversations including Voice over IP conversations, chats, or the like. Labeling for the training set may be performed by a human or by computerized analysis of the data.

Once the data has been preprocessed, it may be further processed and correlated and/or aggregated to obtain evaluation for at least three factors. Each of the factors may have an effect on the pain felt by the patient, such that improving any of the factors may help the patient feel better. For example, the factors may include but are not limited to any one or more of the following: activity level; sleep quality; emotional state; social state; stress level; and pain interference score.

The factor evaluation may also be performed by any engine, including but not limited to AI engines as detailed above, which may be trained using supervised or unsupervised training.

The evaluation of at least one factor may be based on a combination of two or more inputs, whether the inputs have been preprocessed or not. In some embodiments, the same AI engine may be used for assessing multiple factors, while in other embodiments each factor may be assessed by a separate AI engine. Thus, the AI engine(s) may receive as input two or more types of data and predict one or more factor evaluations.

In one example, physical activity may be evident by biological measurements and/or GPS data. For example, a location that changes in a pace of about 2-10 miles/hour may indicate walking/hiking/jogging. The data can be monitored over time to assess, for example, an average or accumulated daily or weekly activity time or intensity. In another example, if a portion of the time in which the user's voice is captured exceeds a predetermined threshold, this may indicate social activity exceeding a predetermined threshold, and similarly for a plurality of messaging sessions in one or more social networks or messaging applications.

On the other hand, the same input may be used in the evaluation of a plurality of factors. For example, biological measurements may be used in the evaluation of sleep quality as well as activity, voice analysis may be used in assessing stress as well as social activity, or the like.

A numeric value indicating an assessment of the pain level of the patient may also be provided which is based on aggregating the evaluations for all factors into a single measure.

A recommendation may then be devised based on the evaluated factors, and the assessed pain level. The recommendation may relate to increasing cognitive activity, increasing physical activity such as yoga or home exercising, changing activity type, increasing social life, or the like.

The obtained factors may be displayed to a user such as a physician, for example in a graphic manner. Multiple types of such representation may be used, such as a pie chart wherein each sector is associated with one factor, and indicates how well the patient scored in this area by the portion of the sector being colored or patterned, the shade, the density of the pattern, or the like; a pie chart wherein each sector is associated with one factor, and indicates how well the patient scored in this area by the shade or the density of a pattern; a histogram wherein each bin is associated with one factor and is sized, shaded or patterned according to how well the patient scored in this area, or the like.

Additionally or alternatively, a textual description may show a numeric or another evaluation for each factor and for the pain level, using for example plain text, text with color coding, size coding, or the like. The recommendation(s) may also be presented to the physician.

Another technical solution of the disclosure comprises repeating the information collection and analysis at one or more points or periods in time after treatment has been applied, to obtain objective feedback about the success of the treatment, such that the treatment may be enhanced or updated to further improve the situation of the patient, or stop a useless or harmful treatment.

Yet another technical solution relates to the whole method and system, including the user interface and presentation of the assessed factors and pain level being implemented on a computing device associated with the patient, thereby providing at least a partial self-help tool, which may be limited by regulations, for example no medications are prescribed without physician supervision and recommendation.

Another technical solution of the disclosed subject matter relates to monitoring the factor evaluations over time. For example, the factors and the pain level may be assessed every hour, two hours, six hours, one day, one week, one month, or the like. In some embodiments, the raw information as collected may be stored over time, however, this may take too much storage space. Thus, in another embodiment, only the preprocessed information may be stored, which may reduce the data volume. In further embodiments, only the factor evaluations and the pain level assessment may be stored for monitoring purposes.

The stored factors may then be displayed in a temporal sequence, such that a trend of the evaluated factors may be observed. Analogously, the pain levels assessed for different points in time may be displayed graphically to observe the changes and/or the effectivity of the treatment.

In some embodiments, any of the information items as obtained may be collected by one or more computing platforms associated with the patient, such as a mobile phone or a wearable device, stored and processed by one or more of the computing platform(s). In other embodiments, any of the information items, with or without preprocessing may be transmitted to a remote computing platform, such as a cloud storage device or cloud computing platform for storage and processing. In further embodiments, a hybrid approach may be applied, in which the information is collected by devices associated with the patient, and the storage and processing is done partly by that computing device and partly by a cloud computing platform.

In some embodiments, a goal may be set to the patient regarding one or more of the factors, such as "increase activity to a certain level". The factor may then be monitored to determine whether or to what degree the goal has been met, and encourage the patient accordingly.

One technical effect of the disclosure provides for objectifying chronic pain and obtaining a personalized and objective pain level estimation system and method. The method and system use objective measurements and do not rely solely on the patient's report, and assess and present various factors affecting the pain level, thereby providing a more accurate and full evaluation of the pain level, such that the treatment, whether suggested by the system or by a physician is likely to be more helpful. Thus, it may be better understood what affects the individual's pain and how to prevent or reduce it, and to measure the effectivity of treatments, medication, and lifestyle tailored to the patient. The disclosure may thus provide for applying a bio-psycho-social model for assessing in an objective manner the pain level of a patent. The more a system and method in accordance with the disclosure are used, they may be further trained, and better insights may be obtained, allowing for higher resolution of unique mechanisms.

Another technical effect of the disclosure provides for monitoring the factors and the pain level over time, thereby repeatedly evaluating the effectivity of the treatment, using feedback from the patient and updated measurements.

The objective evaluation and recommendations may provide for more efficient treatment, less clinic visits and unnecessary tests, medications or treatments, thus leading to less suffering by patients and cost reduction.

Figure 1:
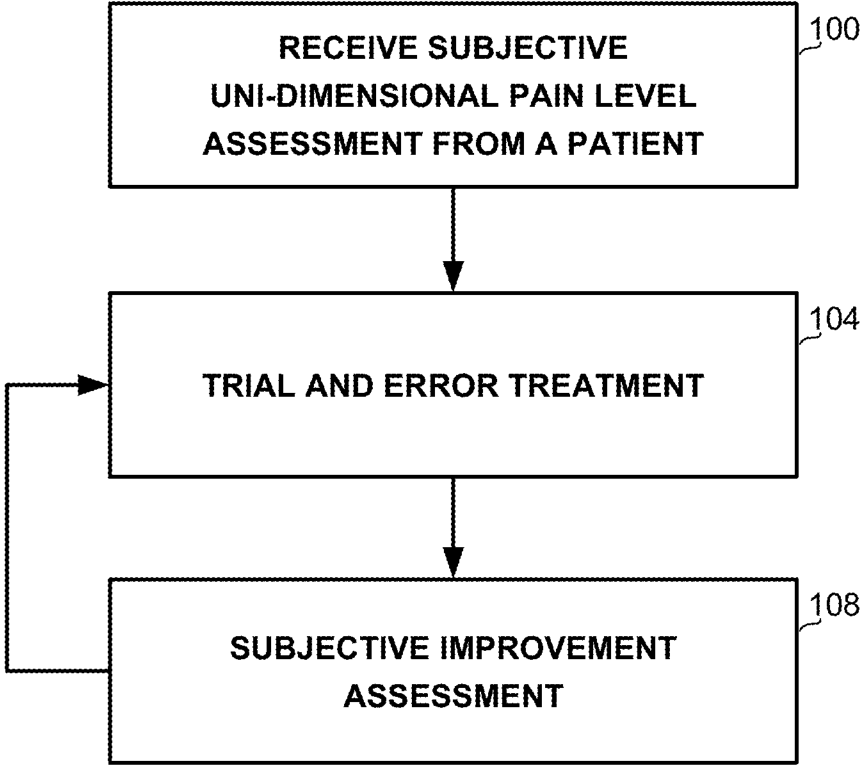
FIG. 1 shows a flowchart diagram of a prior art method for pain level evaluation and monitoring.

Referring now to FIG. 1, showing a flowchart diagram of a prior art method for pain level evaluation and monitoring.

The method is usually applied in cases of chronic rather than acute pains, where there is no recognized cure or solution.

On step 100, a subjective uni-dimensional pain level evaluation is received from a patient. The evaluation n is usually in the form of a number between 0 and 10, optionally with some additional details such as location and description of the pain.

On step 104, a caregiver such as a physician may attempt a treatment for reducing or healing the pain. The treatment may include medication, physical treatment of one or more types such as massage, yoga, walking, stretches, or any other activity, nutritional or lifestyle change, or the like.

On step 108, which may occur a while after step 104, for example one day, one week, one month, three months, or the like, feedback may be received from the patient and an improvement assessment may be performed. The assessment may be similar to the subjective assessment of step 100, and is thus subjective and based solely or mainly on the user's report.

Based on the assessment, step 108 may be repeated where the physician may update the suggested treatment, stop an existing treatment, suggest a new one, or the like, hoping that it will reduce the patient's pain level.

The process may thus continue in a feedback loop where the patient reports the pain level and the physician evaluates the effectivity of the treatment and updates it accordingly.

Figure 2:
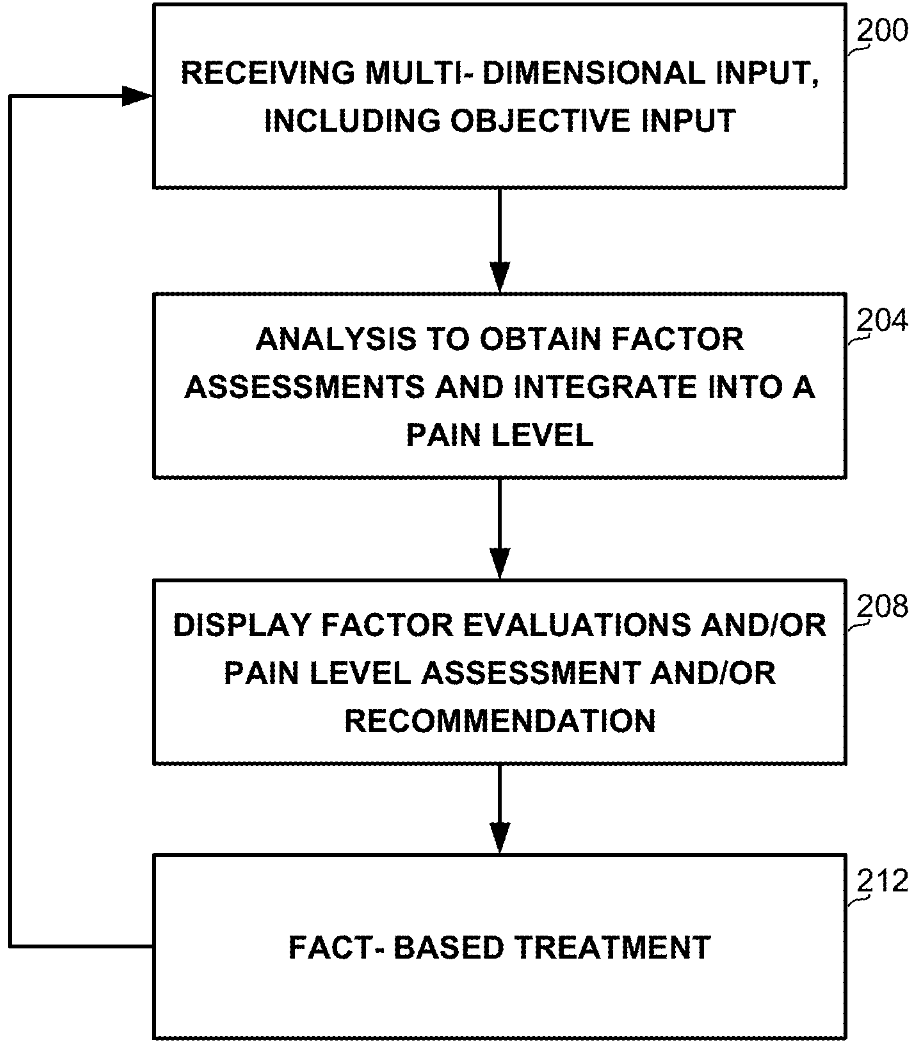
FIG. 2 shows a flowchart diagram of a method for pain level evaluation and monitoring, in accordance with some exemplary embodiments of the disclosed subject matter.

Referring now to FIG. 2, showing a flowchart of steps in a method for pain level evaluation and monitoring, in accordance with some exemplary embodiments of the disclosed subject matter.

On step 200, multi-dimensional input may be received, including both subjective and objective information. The information may be collected prior to visiting the clinic, for example the information collection may begin after a previous visit to a clinic or even earlier. The information may be collected continuously, periodically, or the like, which may also depend on the information type and/or volume.

Figure 3:
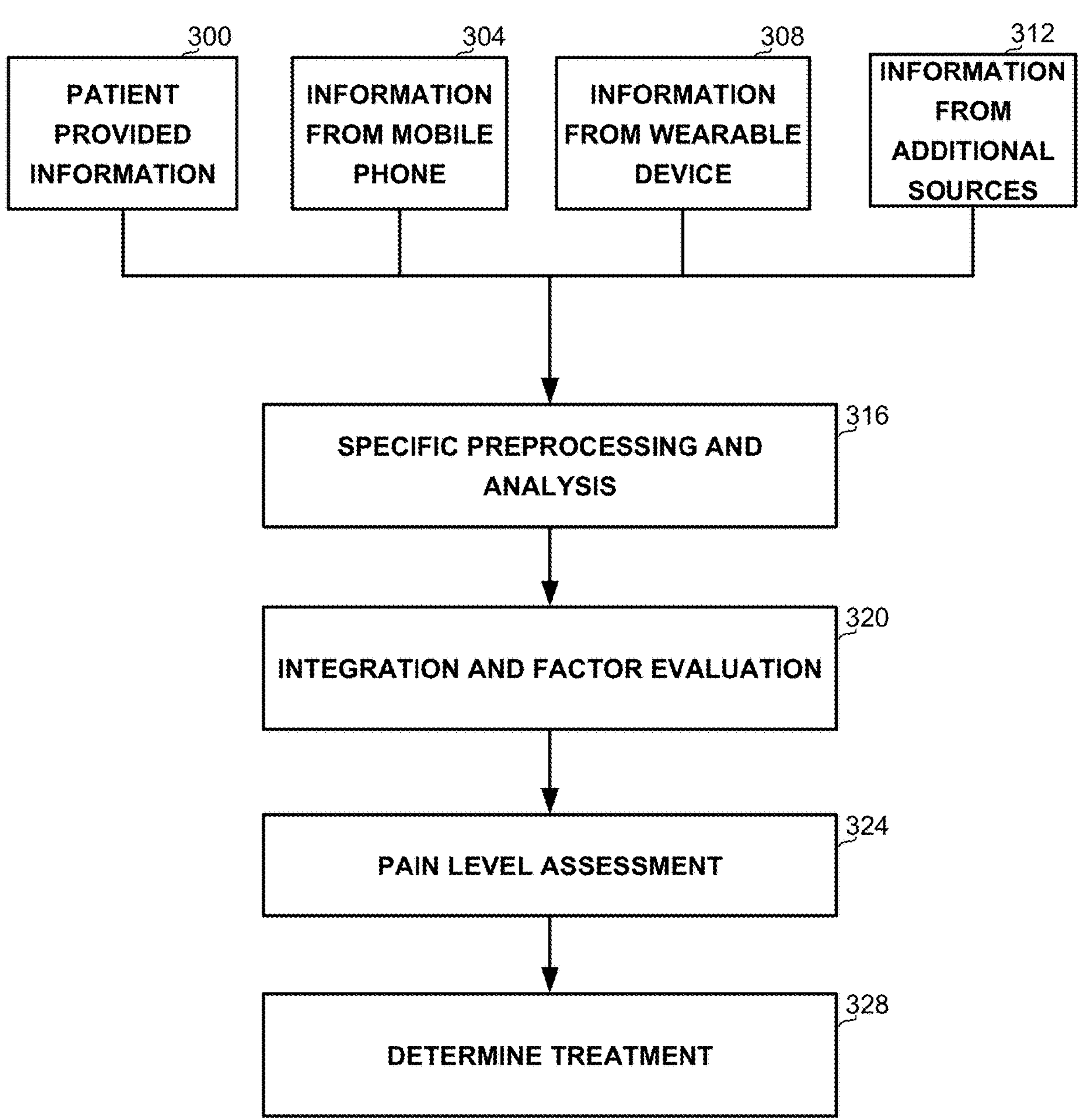
FIG. 3 shows various sources and a method for determining pain level based thereon, in accordance with some exemplary embodiments of the disclosed subject matter.

Referring now also to FIG. 3, showing the various sources and a method for obtaining a pain level based thereon, and to FIG. 4 illustrating various types of the collected information, in accordance with some exemplary embodiments of the disclosed subject matter.

The information sources may include patient provided information 300, which may include patient questionnaire and numerical assessment 400, wherein the assessment may be a numerical assessment of the pain level.

The information may further include information from mobile phone 304, such as phone usage 404 including conversation time, time spent in social networks, time used in other applications which may be defines as utility, content, gaming, or the like, facial capture 408, voice capture 412, location data 416, or the like.

The information may further include information from one or more wearable devices 308, such as sleep data 440, biometric data 424 such as heartbeat or blood pressure measurements, or the like.

The information may further include information from various additional sources 312, such as the Internet, or data collected from the user's activity with a computing platform such as a personal computer, wherein the data may be similar in type to the information collected from the suer's mobile phone.

such as but not limited to social support data 428, cognitive data 432, results of physical examination by a physician or another personnel member 436.

It is appreciated that information may also be captured which is unrelated to the patient, such as air pollution, temperature, humidity, or the like. For example, it is known that temperature changes may impact joint pain, therefore obtaining the temperature may help understand the source of the patient's pain and advise accordingly.

On step 316, some or all of the above information types, and optionally additional types may be preprocessed and analyzed. Each type of information may be preprocessed using a corresponding engine, function, or another tool.

For example facial capture 408 may be preprocessed to enhance the image, and analyzed to identify the patient's mood from the patient's face, voice capture 412 may be preprocessed to remove noise and analyzed to identify emotions such as sadness, happiness, stress, or the like. Location data 416 may be preprocessed to determine whether and when the patient was in motion, and whether this motion can be classified as physical activity (for example advancement in a speed lesser than 10 miles/hour). Sleep data 420 may be analyzed to determine whether the patient completed a personally determined sufficient number of full sleep cycles, whether the patient is sleepy during the day, or the like. Biometric data 424 may be used for identifying effort, irregularities in the heart beat or other parameters, or the like.

Phone usage 404 may be preprocessed and analyzed to evaluate time spent talking on the phone, and if possible the distribution between talking with institutes/facilities, and family/friends; time spent on social networks and if possible distribution between passive (reading) and active (commenting/writing/recording), or the like.

On step 320, the information, whether preprocessed or not as required, may be input into an engine, such as an AI engine, that integrates the information and assesses a plurality of factors which may be relevant to pain assessment. The factors may include but are not limited to any one or more of the following:

Emotional state, which may be for example assessed based on the social support data 428, facial capture 408 as preprocessed, voice capture 412 as captured, sleep data 420 as preprocessed since lack of sleep can significantly affect the emotional state of a patient, or the like.

Social state may be assessed in accordance with preprocessed phone usage data 404, data obtained from the patient's digital accounts as collected from the user's personal computer, voice analysis of voice capture 412 aimed at identifying whether the patient is interacting with another person, or the like.

Stress level may be assessed by analyzing the facial capture 408 as preprocessed, voice analysis of voice capture 412 aimed at identifying whether the voice indicates stress, biometric data 424 that may indicate stress such as high heartbeat, results of physical examination 436, or others.

Pain interference may be assessed from the patient questionnaire optionally as crossed with the activities of the patient. For example, pain interference may indicate how much the pain interferes with the patient's daily activities. The pain interference may be provided subjectively by the patient, and combined with other measurements, for example by tracking the patient's activity, sleep, social engagement or the like.

Activity level may be assessed by analyzing cognitive data 432, location data 416, biometric data 424, phone usage data 404 and optionally additional inputs.

Sleep level may be assessed first by sleep data 420 as analyzed, but may also benefit from other biometric data 424.

It is appreciated that any one or more of the engines above may be trained accordingly. For example, an engine for predicting activity level may be trained upon information from the mobile phone, location data, patent questionnaire and biometric data. Each tuple may be labeled with a corresponding activity label as provided by a user. Once the engine is trained, tuples representing actual data of a patient related to the same types may be input into the engine, and a prediction of the activity level may be obtained.

In some embodiments, the weights used by the engine for combining a plurality of information items into a score may also be set by a user. In further embodiments, the weights may be suggested automatically based on given level, and enhanced by one or more users based on their experience.

It is appreciated that one engine can receive as input all the various types of information, and output a plurality of scores for the different factors. In alternative embodiments, two or more engines may be designed, wherein each engine is trained to receive input of a plurality of types and output a prediction related to one or more factors.

On step 324, a pain level assessment may be obtained upon the various factors as evaluated on step 320. The pain level assessment may be predicted by an AI engine trained to receive as input the various factor evaluations and a label comprising the output pain level. At runtime, also referred to as prediction time, the trained AI engine receives the various assessments and outputs a pain level prediction. In alternative embodiments, the AI engine receives as input the raw or processed data rather than the factor evaluations, and outputs a pain level prediction. In further embodiments, the pain level may be assessed by combining the various features, for example with weights assigned by a human user, or by an automated process and optionally enhanced by a user.

It is appreciated that not all factors necessarily have the same effect on the pain level assessment. Rather, some may have larger effect than others and the effect may also change according to the specific assessment.

On step 328, a treatment recommendation may be determined, for example based also on an AI engine trained on a collection of inputs and factor evaluations, and a label comprising a treatment assigned to the input and evaluations. The engine may then receive combinations of inputs and/or factor assessments and output corresponding treatment recommendations.

On step 208, the factor evaluations and/or the pain level assessment and/or the treatment recommendation may be displayed to a user. The display may be textual, graphic, or the like.

On step 212, the suggested treatment may be recommended to the patient.

The method may then repeat, for receiving updated data and re-assessing the factors, the pain level and the treatment suggestion. When repeating, it may also be verified, for example using patient report (optionally as part of the questionnaire) or a corresponding application, whether and to what degree the patient indeed followed the suggested treatment.

Once the method is repeated two or more times, a comparative view may be displayed, showing the factor assessments in multiple points in time, and the trend of the pain level or the various factors.

Referring now to FIG. 5, showing graphic representations of evaluated factors and assessed pain level, in accordance with some exemplary embodiments of the disclosed subject matter. The factors are shown in a pie chart, wherein each factor is represented as a sector, and its colored area is indicative of the relevant score. Thus, a sector having a large colored area represents a factor in which the patient did better (or worse, according to how the pie is arranged) than in a factor whose relevant score has a smaller colored area. In the example of FIG. 5, the patient did better in "social" factor 504 and in "pain interference" factor 508, than in emotional factor 512 and activity factor 516. The total pain score assessment 520, being 84, is also displayed.

Referring now also to FIG. 6, showing a graphic representation of the evaluated factors and assessed pain level, in accordance with some exemplary embodiments of the disclosed subject matter, as referring to another patient, or the same patient on a different time. Display 600 generally demonstrates larger portions of the pie being colored, and therefore a lower pain level, being 40 as compared to 84 in FIG. 5.

It is appreciated that the representation of FIG. 5 and FIG. 6 are exemplary only, and other representations may be used. For example, the pie chart may indicate the evaluation of each factor using different shades or patterns (for example a darker shade or denser pattern may indicate a higher score) rather than a color portion, In other examples, a different representation may be used, such as a histogram, a three dimensional display, or the like.

Referring now to FIG. 7, showing a block diagram of a system 700 for pain level evaluation and monitoring in accordance with some exemplary embodiments of the disclosed subject matter.

In some exemplary embodiments, system 700 may comprise one or more Processor(s) 704. Processor 704 may be a Central Processing Unit (CPU), a microprocessor, an electronic circuit, an Integrated Circuit (IC) or the like. Processor 704 may be utilized to perform computations required by system 700 or any of its subcomponents.

In some exemplary embodiments of the disclosed subject matter, system 700 may comprise an Input/Output (I/O) device 708. I/O device 708 may be utilized to receive input from a user. Additionally or alternatively, I/O device 708 may be utilized to provide output to a user, such as display the factor evaluation and pain level assessment.

In some exemplary embodiments system 700 may comprise one or more communication components 712, for communicating with other devices, such as a mobile phone or a wearable device associated with the patient, other systems for receiving information, or the like. Communication components 712 may be capable of communicating via any wired or wireless communication channel using any corresponding communication protocol.

In some exemplary embodiments, system 700 may comprise storage device 716. Storage device 716 may be a hard disk drive, a Flash disk, a Random Access Memory (RAM), a memory chip, or the like. In some exemplary embodiments, storage device 716 may retain program code operative to cause processor 704 to perform acts associated with any of the subcomponents of system 700, and steps associated with FIG. 3 and FIG. 4 above.

The components detailed below may be implemented as one or more sets of interrelated computer instructions, executed for example by processor 704 or by another processor. The components may be arranged as one or more executable files, dynamic libraries, static libraries, methods, functions, services, or the like, programmed in any programming language and under any computing environment.

Storage device 712 may comprise user interface 720 for displaying to a user, such as a physician or even the patient, the various factors evaluations, and the pain level assessment. User interface 720 may also display various other data items, such as phone usage and statistics thereof, physical measurements, or the like. User interface 720 may also be operative in displaying a questionnaire to the patient and collecting the patient's responses.

In some embodiments, user interface 720 may be enabled on the patient's mobile phone or another computing device. Additionally or alternatively, user interface 720 may be enabled on a computing platform used by a physician.

Storage device 712 may comprise data obtaining module 724 for obtaining data from sources using communication device 712, for example from the patient's mobile phone or wearable device, receiving data over the Internet, or the like.

Storage device 712 may comprise input processing modules 728 for processing the various input types, for example face analysis, voice analysis, activity analysis or the like, as detailed above.

Storage device 712 may comprise factor evaluation module 732 for evaluation a score for one or more factors, based on the input as received and optionally processed by input processing modules 728. Factor evaluation module 732 may comprise one or more engines, such as AI engines, trained to receive the input of the various types and output evaluations for one or more factors.

Storage device 712 may comprise pain level assessment module 732 for assessing the pain level based on the factor evaluation and/or the inputs.

Storage device 712 may comprise monitoring module 740 for monitoring the factors and pain level over time, presenting them in a comparative manner such as a graph or a histogram, or the like.

Storage device 712 may comprise treatment recommendation module for recommending based on the various factors and/or the assessed pain level a treatment, such as medications, general or specific types of activity, massage, mental relaxation, or the like.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The disclosed subject matter is presented to enable one of ordinary skill in the art to make and use the invention as provided in the context of a particular application and its requirements. Various modifications to the described embodiments will be apparent to those with skill in the art, and the general principles defined herein may be applied to other embodiments. Therefore, the present invention is not intended to be limited to the particular embodiments shown and described, but is to be accorded the widest scope consistent with the principles and novel features herein disclosed. In other instances, well-known methods, procedures, and components have not been described in detail so as not to obscure the present invention.

What is claimed is:

1. A method for monitoring and displaying pain level of a patient, comprising:

obtaining inputs comprising at least:

a patient report of a pain level, a physical activity indicator obtained from at least one wearable device or mobile phone associated with the patient, a sleep indicator obtained from the at least one wearable device or mobile phone, and an objective social activity indicator obtained through a communication channel from the at least one wearable device or mobile phone;

analyzing the inputs to obtain at least three factor evaluations corresponding to at least three factors indicating a wellbeing status of the patient;

integrating the at least three factor evaluations into a pain score assessment based only on data of the patient; and displaying over a computerized display device a graphic presentation of the at least three factor evaluations and the pain score evaluation, wherein the at least three factor evaluations are displayed as a pie chart comprising a sector for each factor evaluation of the at least three factor evaluations.

2. The method of claim 1, wherein an evaluation corresponding to each sector is indicated by a part of the sector that is highlighted, colored, or patterned.

3. The method of claim 1, wherein an evaluation corresponding to each sector is indicated by a shading or pattern of the sector.

4. The method of claim 1, further comprising displaying also the at least three factor evaluations and the pain level evaluation as related to an earlier point in time.

5. The method of claim 1, wherein said analyzing comprises preprocessing at least one of the inputs.

6. The method of claim 1, wherein said analyzing comprises integrating a plurality of inputs into at least one of the at least three factor evaluations.

7. The method of claim 1, wherein the inputs comprise at least one item selected from the group consisting of: phone usage; social network usage; voice recording of the patient; facial captures of the patient; physical examination results; cognitive indicators; biological measurements; and location based information.

8. The method of claim 1, wherein the at least three evaluation comprise at least one item selected from the group consisting of: activity level; sleep quality; emotional state; social state; stress level; and pain interference score.

9. The method of claim 1, wherein analyzing the inputs comprise at least one item selected from the group consisting of: analyzing the voice recording; analyzing the facial captures; analyzing location data; analyzing sleep data; analyzing biometric data; and analyzing phone usage data.

10. The method of claim 1, wherein at least one wearable device comprises a tablet computer or a desktop computer.

11. The method of claim 1, wherein analyzing the inputs comprises activating at least one pre-trained artificial intelligence engine.

12. The method of claim 1, wherein integrating the at least three factor evaluations into a pain score comprises activating at least one pre-trained artificial intelligence engine.

13. The method of claim 1, wherein said obtaining is performed continuously for at least the physical activity indicator.

14. The method of claim 1, further comprising displaying pain trends for the patient, or pain levels of the patient assessed in different points in time.

15. A computerized apparatus having a processor, the processor being adapted to perform the steps of:

obtaining through a communication channel inputs comprising at least:

a patient report of a pain level, a physical activity indicator obtained from at least one wearable device or mobile phone associated with the patient, a sleep indicator obtained from the at least one wearable device or mobile phone, and an objective social activity indicator obtained from the at least one wearable device or mobile phone;

analyzing the inputs to obtain at least three factor evaluations corresponding to at least three factors indicating a wellbeing status of the patient;

integrating the at least three factor evaluations into a pain score assessment based only on data of the patient; and displaying over a computerized display device a graphic presentation of at least three factor evaluations and the pain score evaluation, wherein the at least three factor evaluations are displayed as a histogram comprising a bin associated with each factor evaluation of the at least three factor evaluations, and wherein the bin is sized, shaded or patterned according to an evaluation corresponding to the factor evaluation.

16. A computer program product comprising non-transitory computer program instruction configured, when executed by a processor, to cause the processor to perform:

obtaining through a communication channel inputs comprising at least:

a patient report of a pain level, a physical activity indicator obtained from at least one wearable device or mobile phone associated with the patient, a sleep indicator obtained from the at least one wearable device or mobile phone, and an objective social activity indicator obtained from the at least one wearable device or mobile phone;

analyzing the inputs to obtain at least three factor evaluations corresponding to at least three factors indicating a wellbeing status of the patient;

integrating the at least three factor evaluations into a pain score assessment based only on data of the patient; and displaying over a computerized display device a graphic presentation of at least three factor evaluations and the pain score evaluation, wherein the at least three factor evaluations are displayed as a pie chart comprising a sector for each factor evaluation of the at least three factor evaluations.

* * * * *